United States Patent [19]

Pfister et al.

[11] Patent Number: 4,544,655
[45] Date of Patent: Oct. 1, 1985

[54] ANTIINFLAMMATORY, ANALGESIC, AND ANTIRHEUMATIC 4-HYDROXY-2-METHYL-N-(2-PYRIDYL)-6-TRIFLUOROMETHYL-2H-THIENO[2,3-E]-1,2-THIAZINE-3-CARBOXAMIDE 1,1-DIOXIDE, CORRESPONDING COMPOSITIONS, AND 3-CARBOXYLIC ACID LOWER ALKYL ESTER INTERMEDIATES

[75] Inventors: Rudolf Pfister, Basel; Paul Zeller, Allschwil, both of Switzerland; Dieter Binder; Otto Hromatka, both of Vienna, Austria

[73] Assignee: Hoffmann-La Roche Inc., Nutley, N.J.

[21] Appl. No.: 528,341

[22] Filed: Aug. 31, 1983

[30] Foreign Application Priority Data

Sep. 9, 1982 [CH] Switzerland ............... 5377/82

[51] Int. Cl.$^4$ .................. C07D 513/04; A61K 31/54
[52] U.S. Cl. ............................. 514/222; 544/48
[58] Field of Search .............. 424/246; 544/48; 514/222

[56] References Cited

U.S. PATENT DOCUMENTS 4,076,709  2/1978  Hromatka et al. ............ 544/48
4,180,662  12/1979  Pfister et al. ............... 544/48
4,224,445  9/1980  Hromatka et al. ............ 544/48

OTHER PUBLICATIONS

Harry L. Yale, The Trifluoromethyl Group in Medicinal Chemistry, J Med and Pharm Chem, VI, No. 2, 1959, p. 121.

Primary Examiner—Henry R. Jiles
Assistant Examiner—J. G. Mullins
Attorney, Agent, or Firm—Jon S. Saxe; Bernard S. Leon; Matthew Boxer

[57] ABSTRACT

4-Hydroxy-2-methyl-3-(2-pyridylcarbamoyl)-6-trifluoromethyl-2H-thieno[2,3-e]-1,2-thiazine 1,1-dioxide of the formula

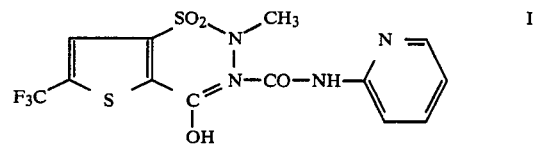

and its pharmaceutically acceptable salts which possess valuable pharmacodynamic properties are described. More particularly, the compound and its salts display antiinflammatory, analgesic and antirheumatic activities and they are readily accessible by reacting a corresponding alkyl ester with 2-aminopyridine and, if desired, subsequent salt formation.

5 Claims, No Drawings

ANTIINFLAMMATORY, ANALGESIC, AND ANTIRHEUMATIC 4-HYDROXY-2-METHYL-N-(2-PYRIDYL)-6-TRIFLUOROMETHYL-2H-THIENO[2,3-E]-1,2-THIAZINE-3-CARBOXAMIDE 1,1-DIOXIDE, CORRESPONDING COMPOSITIONS, AND 3-CARBOXYLIC ACID LOWER ALKYL ESTER INTERMEDIATES

BRIEF SUMMARY OF THE INVENTION

The invention relates to thiazine derivatives. More particularly, the invention relates to 4-hydroxy-2-methyl-3-(2-pyridylcarbamoyl)-6-trifluoromethyl-2H-thieno[2,3-e]-1,2-thiazine 1,1-dioxide of the formula

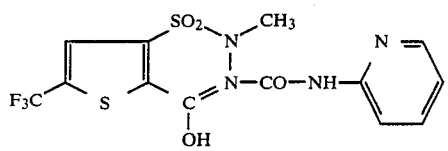

and pharmaceutically acceptable salts thereof. The compound of formula I and its salts are useful as antiinflammatory, analgesic and antirheumatic agents.

In another aspect the invention relates to intermediates of the formula

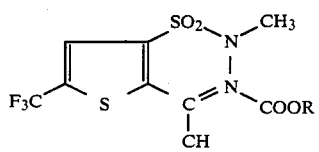

wherein R is lower alkyl.

In yet another aspect the invention relates to a process for the preparation of the compound of formula I.

DETAILED DESCRIPTION OF THE INVENTION

The invention relates to thiazine derivatives. More particularly, the invention relates to 4-hydroxy-2-methyl-3-(2-pyridylcarbamoyl)-6-trifluoromethyl-2H-thieno[2,3-e]-1,2-thiazine 1,1-dioxide of the formula

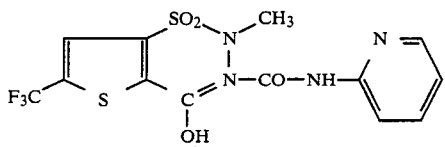

Objects of the invention are the compound of formula I and pharmaceutically acceptable salts thereof, the manufacture of said substances and intermediates for their manufacture, medicaments containing such substances and the manufacture of such medicaments, as well as the use of the compound of formula I or its pharmaceutically acceptable salts in the control or prevention of illnesses.

As used herein, the term "lower alkyl" denotes straight-chain or branched saturated hydrocarbon groups containing 1-7 carbon atoms such as methyl, ethyl and the like.

The compound of formula I and its pharmaceutically acceptable salts can be prepared in accordance with the invention by reacting a compound of the formula

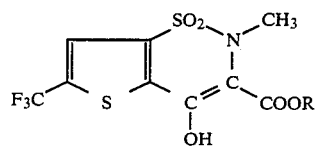

wherein R is lower alkyl,
with 2-aminopyridine and, if desired, converting the compound of formula I obtained into a desired pharmaceutically acceptable salt.

The reaction of a compound of formula II with 2-aminopyridine can be carried out with or without an inert solvent. Suitable solvents are hydrocarbons such as benzene, toluene, xylene or the like; halogenated hydrocarbons such as chloroform, chlorobenzene, methylene chloride, carbon tetrachloride or the like; dimethylformamide or dioxane. The reaction is preferably carried out while heating. The melting temperature or reflux temperature of the reaction mixture is especially preferred.

The compounds of formula II also form part of the invention. Said compounds can be prepared, for example, starting from compounds of the formula

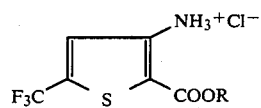

wherein R is as previously described,
which belong to a class of known substances, in accordance with the Reaction Scheme I and the specific Example which follow:

Reaction Scheme I

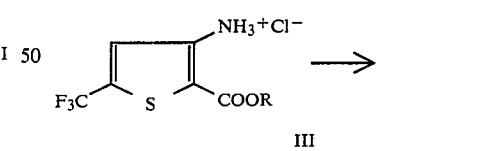

III

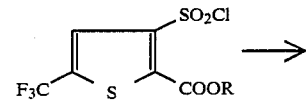

IV

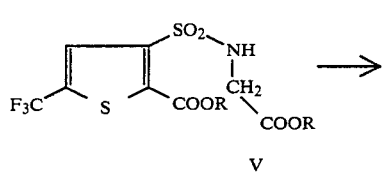

V

-continued
Reaction Scheme I

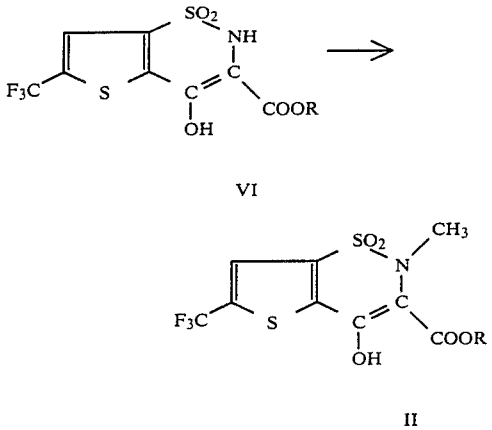

The compound of formula I contains an acidic hydrogen atom and can form pharmaceutically acceptable salts with bases. Such salts include, for example, alkali metal salts such as lithium, sodium or potassium salts; alkaline earth metal salts such as magnesium or calcium salts; salts with amines such as triethanolamine, diethylaminoethanol, triethylamine, trimethylamine or diethylamine; and the like. The compound of formula I can also form pharmaceutically acceptable acid addition salts with strong acids, especially with mineral acids such as hydrochloric acid.

The compound of formula I and its pharmaceutically acceptable salts possess antiinflammatory, analgesic and antirheumatic activities. These valuable pharmacological properties can be demonstrated using standard methods, for example, the known carrageenin paw oedema test on rats. In this test, an acute local inflammation is produced in the right hind paw of the rat by the intradermal injection of 0.1 ml of a 5 percent carrageenin solution. The substance under investigation is administered orally and the diameter of the paw is measured in mm (as an expression of the severity of the inflammation).

The substance to be tested is administered after the carrageenin injection and the paw diameter is measured 2, 3 and 4 hours after the carrageenin injection. The edema-inhibiting effect is determined on the bases of the difference of the edema intensity between untreated animals and animals treated with the test substance. The $ED_{30}$ is that dosage which is required to reduce by 30% the diameter of the paw which is inflamed by the carrageenin injection. An $ED_{30}$ of 1.91 mg/kg p.o. was obtained with the compound of formula I.

The compound of formula I has an activity which is qualitatively similar to that of phenylbutazone which is known for its therapeutic use and properties.

The compound of formula I and its pharmaceutically acceptable salts can be used as medicaments; for example, in the form of pharmaceutical preparations which contain them in admixture with a pharmaceutical organic or inorganic inert carrier material which is suitable for enteral or parenteral administration such as, for example, water, gelatine, gum arabic, lactose, starch, magnesium stereate, talc, vegetable oils, polyalkylene glycols, petroleum jelly and the like. The pharmaceutical preparations can be made up in a solid form, for example, as tablets, dragees, suppositories or capsules, in a semi-solid form, for example, as salves, or in a liquid form, for example as solutions, suspensions or emulsions. If desired, the pharmaceutical preparations can be sterilized and/or can contain adjuvants such as preserving, stabilizing or emulsifying agents, salts for varying the osmotic pressure or buffers. They can also contain still other therapeutically valuable substances.

As mentioned earlier, the compound of formula I and its pharmaceutically acceptable salts can be used in accordance with the invention in the control or prevention of illnesses, especially in the control or prevention of inflammations, pains and rheumatic illnesses. The dosage at which the compound of formula I and its pharmaceutically acceptable salts can be administered can vary within fairly wide limits and is, of course, fitted to the individual requirements in each particular case. In general, in the case of warm blooded animals an oral daily dosage of about 5 mg to about 100 mg, preferably about 10 mg to about 30 mg can be utilized.

The medicaments containing the compound of formula I or a pharmaceutically acceptable salt thereof are also an object of the present invention, as is a process for the preparation of such medicaments, which process comprises compounding the compound of formula I or a pharmaceutically acceptable salt thereof and, if desired, one or more other therapeutically valuable substances into a galenical form.

The Examples which follow, in which all temperatures are given in degrees Centigrade, further illustrate the invention:

EXAMPLE 1

Preparation of 4-hydroxy-2-methyl-3-(2-pyridylcarbamoyl)-6-trifluoromethyl-2H-thienol[2,3,e]-1,2-thiazine 1,1 dioxide.

(a) A solution of 172 g of crude ethyl 3-amino-5-trifluoromethyl-thiophene-2-carboxylate hydrochloride [Monatshefte f. Chemie 105, 132 (1974)] in a small amount of water is made alkaline with sodium hydrogen carbonate and the precipitated material is extracted three times with 300 ml of methylene chloride each time. The combined organic extracts are dried over sodium sulfate and evaporated.

The thus-obtained free base (102 g) is treated with a solution of 2 g of sodium in 800 ml of absolute methanol and the solution obtained is heated to boiling under reflux for 40 minutes. After cooling, 6 ml of glacial acetic acid are added thereto, the methanol is largely removed in vacuo and the residue is partitioned between methylene chloride and saturated sodium bicarbonate solution. The organic phase is separated, dried over sodium sulphate and evaporated. In order to remove the residual methylene chloride, the oily residue is evaporated twice with benzene and then taken up in 600 ml of absolute benzene. The solution is treated with three teaspoons of active carbon, filtered under suction and hydrogen chloride gas is introduced into the filtrate until the precipitation is complete. The colorless crystalline methyl 3-amino-5-trifluoromethyl-thiophene-2-carboxylate hydrochloride removed by filtration under suction, washed with benzene and dried in the air.

(b) 5.60 g of methyl 3-amino-5-trifluoromethyl-thiophene-2-carboxylate hydrochloride are introduced portionwise at −2° and while stirring into 11.3 ml of concentrated hydrochloric acid, a thick paste resulting. Then, at −5° to 0°, a solution of 1.51 g of sodium nitrite in 2.7 ml of water is introduced below the surface of the suspension during 1.5 hours, the mixture becoming fluid towards the end of the addition. The mixture is stirred at −3° for an additional 1 hour, whereupon the solution of the diazonium salt obtained is added in one portion to a mixture of 2.4 ml of saturated copper (II) chloride solution and 38 ml of 30 percent sulfur dioxide solution in glacial acetic acid, intense foaming occurring immediately. The mixture is stirred at room temperature for an additional 1 hour, then poured into 70 ml of ice-water and the separated oil is extracted five times with 50 ml of methylene chloride each time. The combined organic extracts are washed three times with 25 ml of water each time, dried over sodium sulfate and evaporated in vacuo. The oily residue, consisting of methyl 3-chlorosulfonyl-5-trifluoromethyl-thiophene-2-carboxylate, is used in the next step without additional purification.

(c) 103.8 g of methyl 3-chlorosulfonyl-5-trifluoromethyl-thiophene-2-carboxylate are dissolved in 600 ml of chloroform, 68.05 g of freshly distilled methyl glycinate are added dropwise thereto in a manner such that the temperature does not exceed 30°, the mixture is stirred at room temperature for an additional 0.5 hour and then extracted three times with 200 ml of 1N hydrochloric acid each time. The organic phase is dried over sodium sulfate and evaporated. The oily residue is stirred with 175 ml of diisopropyl ether, and there is obtained methyl 3-[(methoxycarbonylmethyl)sulfamoyl]-5-trifluoromethyl-thiophene-2-carboxylate in the form of colorless crystals which are removed by filtration under suction and washed with diisopropyl ether. The product melts at 76°–78° after recrystallization from diisopropyl ether.

(d) A solution of 82.8 g of methyl 3-[(methoxycarbonylmethyl)sulfamoyl]-5-trifluoromethyl-thiopene-2-carboxylate in 1.7 l of absolute tetrahydrofuran is cooled to 3° and treated portionwise at this temperature for 20 minutes with a total of 62.9 g of potassium tert-.butylate. Thereafter, the cooling bath is removed, the viscous red paste is stirred at room temperature for 2 hours and then as much tetrahydrofuran as possible is distilled off in vacuo at a maximum temperature of 30°. The powdery residue is taken up in 1.4 l of ice-water, treated with 10 g of active carbon while stirring and suction filtered over siliceous earth. The filtrate is adjusted to pH 2–3 with about 185 ml of 3N hydrochloric acid at a maximum temperature of 5°. The mixture is stirred for 0.5 hour, whereupon the crude product which initially separates in the form of an oil crystallizes (after the addition of ether). The precipitated crude product is removed by filtration under suction, washed neutral with water, dried at 50° overnight in vacuo and recrystallized from methanol. 4-Hydroxy-3-methoxycarbonyl-6-trifluoromethyl-2H-thieno[2,3-e]-1,2-thiazine 1,1-dioxide of melting point 168°–170° is obtained.

(e) A solution, cooled to −2°, of 5.65 g of 4-hydroxy-3-methoxycarbonyl-6-trifluoromethyl-2H-thieno[2,3-e]-1,2-thiazine 1,1-dioxide in 62 ml of absolute dimethylformamide is treated portionwise under a strong nitrogen stream with 0.87 g of sodium hydride (washed with benzene), the mixture is stirred at 5° for an additional 1.5 hours, then 1.49 ml of methyl iodide are added thereto in one portion, the temperature rising to about 15°. The mixture is stirred at room temperature for an additional 1.5 hours and then evaporated in vacuo. The residue is partitioned between 2N hydrochloric acid and methylene chloride, the aqueous phase is extracted three times with methylene chloride, the combined organic extracts are dried over sodium sulfate and evaporated. The brown crystalline residue is digested with about 50 ml of ethanol, the almost colorless crystals are removed by filtration under suction and washed with methanol. After recrystallization from ethanol, there is obtained 4-hydroxy-3-methoxycarbonyl-2-methyl-6-trifluoromethyl-2H-thieno[2,3-e]-1,2-thiazine 1,1-dioxide of melting point 178°–180°.

(f) 4.25 g of 4-hydroxy-3-methoxycarbonyl-2-methyl-6-trifluoromethyl-2H-thieno[2,3-e]-1,2-thiazine 1,1-dioxide are heated to boiling under reflux for 5 hours while stirring together with 1.54 g of 2-aminopyridine in 192 ml of xylene, solvent is distilled slowly and being replaced by fresh xylene. The mixture is subsequently evaporated in vacuo, the semi-crystalline residue is digested in about 40 ml of dioxane and the yellow crystals obtained are removed by filtration suction and washed with dioxane. The crude product is partitioned between 30 ml of methylene chloride and 40 ml of water which contains 3 ml of 10 percent sodium hydroxide solution. The phases are separated. The aqueous phase is treated with 0.5 g of active carbon and filtered through siliceous earth. The filtrate is warmed to 30° and adjusted to pH 2 with about 2.7 ml of 3N hydrochloric acid (while stirring for 1 hour). The precipitated fine yellow crystals are removed by filtration under suction, washed well with water and dried at 105° for 8 hours in a high vacuum (0.1 mm) 4-Hydroxy-2-methyl-3-(2-pyridylcarbamoyl)-6-trifluoromethyl-2H-thieno[2,3-e]-1,2-thiazine 1,1-dioxide of melting point 230° (decomposition) is obtained.

EXAMPLE 2

Suppositories of the following composition are prepared in the usual manner:

| | |
|---|---|
| 4-Hydroxy-2-methyl-3-(2-pyridylcarbamoyl)-6-trifluoromethyl-2H—thieno[2,3-e]-1,2-thiazine 1,1-dioxide | 0.005 g |
| Hydrogenated coconut oil | 1.250 g |
| Carnauba wax | 0.045 g |

EXAMPLE 3

Tablets of the following composition are prepared in the usual manner:

| | Per tablet |
|---|---|
| 4-Hydroxy-2-methyl-3-(2-pyridylcarbamoyl)-6-trifluoromethyl-2H—thieno[2,3-e]-1,2-thiazine 1,1-dioxide | 5.00 mg |
| Lactose | 84.50 mg |
| Maize starch | 10.00 mg |
| Magnesium stearate | 0.50 mg |

EXAMPLE 4

Capsules containing the following ingredients are prepared in the usual manner:

| | Per Capsule |
|---|---|
| 4-Hydroxy-2-methyl-3-(2-pyridylcarbamoyl)-6-trifluoromethyl-2H—thieno[2,3-e]-1,2-thiazine 1,1-dioxide | 10 mg |

| -continued | |
| --- | --- |
| | Per Capsule |
| Lactose | 165 mg |
| Maize starch | 30 mg |
| Talc | 5 mg |
| Total weight | 210 mg |

We claim:

1. 4-Hydroxy-2-methyl-3-(2-pyridylcarbamoyl)-6-trifluoromethyl-2H-thieno[2,3-e]-1,2-thiazine 1,1-dioxide of the formula

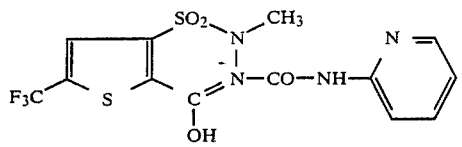

or a pharmaceutically acceptable salt thereof.

2. A compound of the formula

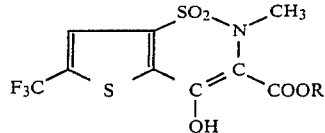

wherein R is lower alkyl.

3. An antiinflammatory composition consisting of an antiinflammatorily effective amount of 4-hydroxy-2-methyl-3-(2-pyridylcarbamoyl)-6-trifluoromethyl-2H-thieno[2,3-e]-1,2-thiazine 1,1-dioxide or a pharmaceutically acceptable salt thereof and a pharmaceutically acceptable inert carrier.

4. An analgesic composition consisting of an analgesically effective amount of 4-hydroxy-2-methyl-3-(2-pyridylcarbamoyl)-6-trifluoromethyl-2H-thieno[2,3-e]-1,2-thiazine 1,1-dioxide or a pharmaceutically acceptable salt thereof and an inert carrier.

5. An antirheumatic composition consisting of an antirheumatically effective amount of 4-hydroxy-2-methyl-3-(2-pyridylcarbamoyl)-6-trifluoromethyl-2H-thieno[2,3-e]-1,2-thiazine 1,1-dioxide or a pharmaceutically acceptable salt thereof and an inert carrier.

* * * * *